United States Patent [19]

Shenoy et al.

[11] Patent Number: 4,556,404
[45] Date of Patent: Dec. 3, 1985

[54] SPLIT-COLUMN EXTRACTIVE DISTILLATION

[75] Inventors: Thirthahalli A. Shenoy, Whitehall; Martha S. Losin, Emmaus, both of Pa.

[73] Assignee: Air Products and Chemicals, Inc., Allentown, Pa.

[21] Appl. No.: 652,231

[22] Filed: Sep. 19, 1984

[51] Int. Cl.$^4$ ............................................. F25J 3/02
[52] U.S. Cl. ........................................ 62/17; 62/20; 62/28; 62/30; 62/42; 202/154
[58] Field of Search ............... 62/17, 20, 24, 26–33, 62/36, 41, 42; 203/42, 50, 57, 73, 84; 202/154

[56] References Cited

U.S. PATENT DOCUMENTS

| | | | |
|---|---|---|---|
| 2,901,404 | 8/1959 | Kirshenbaum et al. | 203/50 |
| 4,137,129 | 1/1979 | Bjorklund | 62/26 |
| 4,293,322 | 10/1981 | Ryan et al. | 62/17 |
| 4,318,723 | 3/1982 | Holmes et al. | 62/20 |
| 4,383,842 | 5/1983 | O'Brien | 62/20 |
| 4,415,443 | 11/1983 | Murphy | 203/73 |
| 4,428,759 | 1/1984 | Ryan et al. | 62/17 |

FOREIGN PATENT DOCUMENTS 975041  11/1982  U.S.S.R. .

Primary Examiner—S. Leon Bashore
Assistant Examiner—Andrew J. Anderson
Attorney, Agent, or Firm—Geoffrey L. Chase; E. Eugene Innis; James C. Simmons

[57] ABSTRACT

The present invention is directed to an extractive distillation separatory technique wherein the improvement comprises a two stage column with a condenser only for the high pressure section and a reboiler only for the low pressure section, as well as a flash separation of a stream communicating between the sections.

11 Claims, 1 Drawing Figure

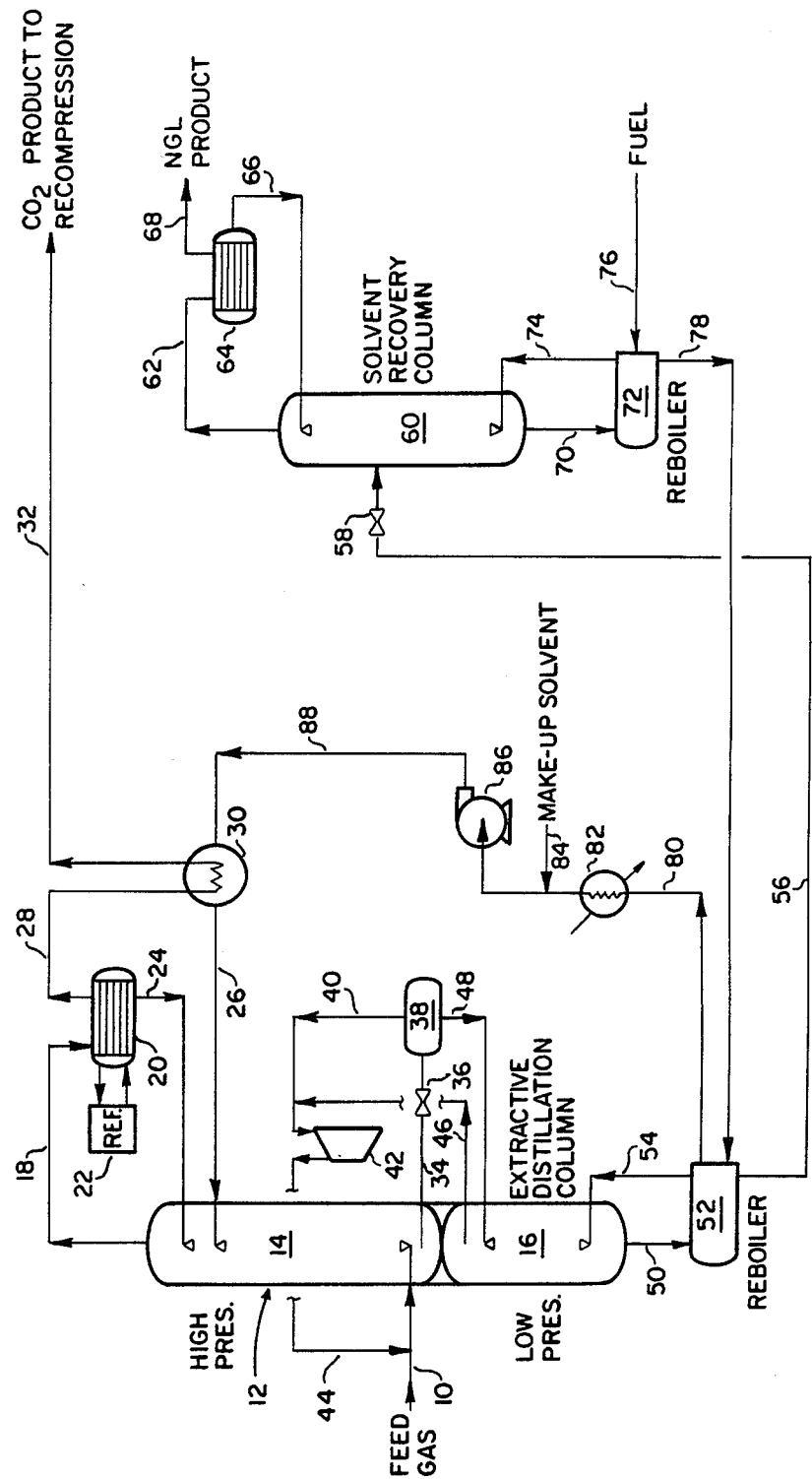

SPLIT-COLUMN EXTRACTIVE DISTILLATION

TECHNICAL FIELD

The present invention is directed to a separatory technique involving distillation in conjunction with extraction with a solvent in a distillation column. In a more specific aspect, the present invention is directed to extractive distillation using a high and low pressure column in order to separate hydrocarbon containing streams into a light stream and a heavy stream with regard to volatility and molecular weight.

BACKGROUND OF THE PRIOR ART

The design of various separatory techniques has become necessary in order to provide more specific and more efficient separations of hydrocarbons produced in less desirable or less naturally producing hydrocarbon reservoirs. With the continual diminishment of hydrocarbon reserves, the industry has gone to the use of enhanced oil recovery techniques. These enhanced techniques include such methods as subjecting low pressure petroleum reservoirs to nitrogen or carbon dioxide pressurized gas injection and oxygen fire flooding. When using a pressurizing medium or a miscibility enhancing meduim, the produced petroleum contains varying amounts of the medium used for production or pressure maintenance purposes. It is desirable to separate the injected medium from the produced petroleum and hydrocarbons. Typically, the high molecular weight liquid petroleum is easily separated from the injected medium, but the lighter hydrocarbons are difficult to separate from the injection medium. Particularly, $C_1$-$C_7$ range hydrocarbons are generally hard to dissociate from the injection medium, such as carbon dioxide. Carbon dioxide is extremely difficult to separate from the very low molecular weight hydrocarbons such as methane, ethane and propane. Additionally, carbon dioxide forms an azeotrope with ethane which makes separation even more difficult for these components. The separation of methane from carbon dioxide is hampered by carbon dioxide freezing problems due to the necessary refrigeration required for the separation of methane.

Various techniques have been developed for the separation of producing mediums, such as carbon dioxide and nitrogen from valuable paraffinic hydrocarbons, such as the $C_1$-$C_7$ range hydrocarbons. Refrigerated distillation is the most evident technique for separating hydrocarbons from mediums such as carbon dioxide. Refrigeration is used to provide a reflux in a distillation column to enhance the separation of the feed gas into a carbon dioxide overhead and a heavy hydrocarbon bottom stream. This technique suffers from the requirement of permissible carbon dioxide loss in the hydrocarbon product and high energy use as the amount of hydrocarbon recovery is raised to a high level.

Another technique designed to overcome the problem of hydrocarbon separation is activated methyldiethanolamine (MDEA). This process uses solvent in a two column scheme to separate $CO_2$ as the bulk component from a produced hydrocarbon gas. The carbon dioxide is then recovered at low pressures, while the hydrocarbon gas remains pressurized. This process is very energy intensive because the carbon dioxide has to be recompressed to high pressures. Capital cost is also increased because of the necessity of a carbon dioxide compressor for enhanced recovery applications in which the carbon dioxide is reinjected into the producing formation.

It is also known to use a membrane process which takes advantage of the different rates of permeation between carbon dioxide and produced hydrocarbons to effect separation. Here again, while the feed is pressurized, the carbon dioxide is recovered as a low pressure product and has to be recompressed, making the process energy intensive. The addition of a compressor to the membrane process also makes the total process capital intensive.

Finally, various extractive distillation techniques are known and are generally referred to as Ryan-Holmes. This Ryan-Holmes technique is exemplified by U.S. Pat. No. 4,293,322, U.S. Pat. No. 4,318,723, U.S. Pat. No. 4,383,842, and U.S. Pat. No. 4,428,759. The latter patent discloses the use of extractive distillation using a $C_3$-$C_6$ extractive solvent in a single column distillation process. Carbon dioxide is separated from various hydrocarbons and inerts, as well as hydrogen sulfide. In FIG. 3 of that patent, an extractive separation technique is set forth wherein carbon dioxide and ethane is separated from propane and higher hydrocarbons. The single extractive distillation column operates with a reboiler and condenser and the distillation column is supplied with solvent from a stripping column wherein the solvent is passed directly to the overhead or condenser of the distillation column without thermodynamic interaction of the various separation stages.

In contrast to the use of lower alkyl hydrocarbons as an extractant medium, such as in the Ryan-Holmes process, in USSR 975041 of Nov. 23, 1982, a technique for separation of carbon dioxide from hydrocarbons is set forth using various siloxanes. The method is particularly useful for separations wherein carbon dioxide constitutes over 60% of the gas mixture being treated.

The present invention overcomes the problems of the prior art in making a separation of hydrocarbons coproduced with petroleum using inert production media, such as carbon dioxide and nitrogen by providing a technique which is energy efficient and capital efficient and yet still effects the difficult separations of such gas species as carbon dioxide and propane.

BRIEF SUMMARY OF THE INVENTION

The present invention constitutes a method for the extractive distillation of a feed gas stream into several products comprising the steps of introducing a feed gas containing multiple separable components into the high pressure section of a two pressure section extractive distillation column, contacting the feed gas with an extractive solvent to assist in the separation of the multiple components of the gas, cooling the overhead of said high pressure section to condense a liquid phase reflux to the high pressure section of the column and to recover a substantial pure light component product stream, removing a bottom stream from said high pressure section and reducing the pressure of said bottom stream to phase separate a vapor reboil stream to said high pressure section and a liquid reflux feed stream to a low pressure section of said column, introducing said liquid reflux feed stream into the low pressure section of said two pressure section extractive distillation column, removing a light component stream from the overhead of said low pressure section and repressurizing the same and introducing it into the high pressure section, reboiling said low pressure section by heat exchange with said extractive solvent in order to provide vapor reboil for said low pressure section and a liquid heavy component solvent stream and introducing the heavy component solvent stream into a second column and separating the heavy components as a product and the solvent as a recycle extractive solvent to the two pressure section extractive distillation column.

Preferably the method is utilized for the separation of carbon dioxide from hydrocarbons wherein the separation is between: (1) propane and higher hydrocarbons, and (2) carbon dioxide potentially with methane and ethane and residual propane therein.

Preferably the extractive solvent used for the separation includes $C_3$–$C_8$ hydrocarbons, as well as various silicon containing hydrocarbons, such as siloxanes. The solvent may be mixtures of these compounds preferably with a primary content of siloxane.

Optimally, the high pressure section of the extractive distillation column is at a pressure in the range of 250 to 500 psia, while the pressure of the low pressure section of the distillation column is in a range of 50 to 300 psia.

Preferably, in warming the low pressure bottom stream with extractive solvent, the regenerated solvent from the second column is directed through the reboiler of the low pressure section of the extractive distillation column in indirect heat exchange with the reboiler in order to provide the necessary heat for the reboiling function, before the solvent is then directed to the upper zone of the high pressure section of the extractive distillation column.

Further, it is preferred that the light component stream from the low pressure section is mixed with the vapor reboil stream to the high pressure section and the combined streams are pressurized to the pressure of the high pressure section before the combined stream is introduced into the high pressure section.

The present invention is also directed to apparatus for the extractive distillation of a multicomponent feed gas stream into a light component product and a heavy component product comprising, an extractive distillation column with a high pressure section and a low pressure section, a condenser for the high pressure section, a reboiler for the low pressure section, means for flashing and separating a reboil stream for the high pressure section and a reflux stream for the low pressure section, a second column for separating extractive solvent from heavy component product and means for circulating extractive solvent from said second column through said reboiler in indirect heat exchange and to said extractive distillation column.

Preferably the apparatus includes means for removing light component from the overhead of the low pressure section and introducing the same into the high pressure section.

BRIEF DESCRIPTION OF THE DRAWING

The FIGURE is a schematic representation of the process of the present invention in its preferred embodiment.

DETAILED DESCRIPTION OF THE INVENTION

The present process uses a split column extractive distillation with a condenser only for the high pressure column and a reboiler only for the low pressure column wherein the reboiler is thermally connected to the reboiler of a solvent recovery column and the bottom stream from the high pressure extractive distillation column is flashed and phase separated into reflux for the low pressure section and feed or reboil for the high pressure section in order to provide a system which has unique efficiencies, both process and capital, in the separation of components of a multicomponent stream that have similar volatilities. These aspects of the present invention allow it to overcome the problem of gas separations, such as the separation of carbon dioxide and $C_1$ and $C_2$ hydrocarbons from $C_3$ and higher hydrocarbons.

The use of a split extractive distillation column with a condenser only in the upper high pressure section of the column and a reboiler only in the lower low pressure section of the column permits the condenser to operate at a higher temperature because of the higher pressure in the condenser thus saving on refrigeration power, while simultaneously permitting the reboiler to operate at a lower temperature and lower duty due to the lower pressure in the reboiler thus saving on heat energy input. Overall, a significant energy savings is possible.

The use of the intermediate flash step between the high pressure section and the low pressure section of the extractive distillation column, which strips a large fraction of the carbon dioxide and lighter gas such as $C_1$ and $C_2$ out of the liquid phase, reduces the temperature and heating load on the reboiler to the low pressure section. Further, since the flash is done at lower temperatures than a corresponding reboil, the removal of $C_3$ and higher hydrocarbons is minimized, thus increasing the recovery of these in the liquid leaving the reboiler. In conventional practice, all the $CO_2$ and lighter gases would have been stripped out from the liquid phase in the reboiler. Because of the higher temperatures in conventional practice, an increased amount of $C_3$ and higher hydrocarbons would have been vaporized, thus reducing the recovery of these hydrocarbons in the liquid phase compared to the present invention.

The use of hot lean solvent to operate the reboiler to the low pressure section of the extractive distillation column reduces the total energy required to operate the system. This is made possible because of the favorable temperature differences and heat duties between the lean solvent and the streams in the reboiler to the low pressure section of the extractive distillation column.

These attributes are achieved with the split column wherein the high pressure section operates at about 250–500 psia and the low pressure section operates at about 50–300 psia.

The present invention will now be described in greater detail with regard to a specific preferred embodiment of the invention directed to the separation of carbon dioxide along with methane and ethane from propane and higher hydrocarbons in a stream produced from an enhanced oil recovery operation wherein carbon dioxide has been used as a pressurizing and miscibility agent in the petroleum reservoir to increase or enhance the recovery of petroleum and hydrocarbons from the reservoir. The produced petroleum or hydrocarbons have a carbon dioxide content which increases generally with the passage of time over which the reservoir has been produced before declining in carbon dioxide content. The liquid petroleum is readily separated from the attendant gases and the present invention is directed to the separation of those attendant gases into carbon dioxide for reinjection preferably into the enhanced recovery operation and heavier hydrocarbon gases and light liquids, such as propane and higher hydrocarbons. The desired cut would effect a separation of carbon dioxide, methane and ethane as a light component product and propane and higher hydrocarbons as a heavy component product.

With reference to the drawing, a feed gas from an enhanced oil recovery operation containing significant amounts of carbon dioxide and gaseous and potentially liquid hydrocarbons is introduced in line 10. A process stream 44 comprising the recompressed overhead from the low pressure column 16 and the reflux from the high pressure column 14 is introduced into the feed gas 10 before the feed gas mixture is introduced into the extractive distillation column 12 in the high pressure section 14. The feed gas is subject to separation under low temperature distillation conditions in the column, which preferably has a series of trays or packing as is typical in a distillation column. The feed gas is also subject to the action of solvent introduced in line 26, which constitutes the extractive distillation nature of the separation herein. The solvent emanating from line 26 in the high pressure section 14 acts to effect a displacement in the volatilities in the components of the feed gas. An overhead vapor stream comprising predominantly carbon dioxide and light hydrocarbons, such as methane and ethane, and potentially propane and other hydrocarbons, is removed in line 18 and is subject to a mild and partial condensation in condenser 20 operated by a refrigeration unit 22. The condenser can operate under mild circumstances due to the high pressure of the column section 14 which keeps the lower volatile components closer to their liquid state. The lighter components, having higher volatility, readily pass through condenser 20 and become product in line 28, while the heavier components, having lower volatility, are returned in line 24 to the high pressure section 14 of the column 12 as reflux.

The product comprising predominantly carbon dioxide with minor amounts of methane and ethane and potentially some residual propane in line 28 is rewarmed in heat exchanger 30 against the incoming extractive solvent before being removed as product in line 32 for sale or recompression and introduction back into an enhanced oil recovery operation.

The bottom stream which collects in the base of high pressure section 14 is removed in line 34 and is reduced in pressure quickly through a valve in order to flash the stream into phase separation vessel 38. Light components having high volatility are removed as a gas phase in line 40, while heavy components having low volatility are removed as a liquid phase in line 48 and introduced into the low pressure section 16 of the column 12 as reflux. Overhead vapor in the low pressure section 16 of the column 12 is removed in line 46 and is combined with the stream in line 40 after which the combined stream is recompressed in compressor 42 to the pressure of the high pressure section 14 before being introduced into the feed gas by way of line 44.

This intermediate flash stage avoids the use of a condenser for the low pressure section 16 and a reboiler for the high pressure section 14 while still providing for liquid reflux for the low pressure section 16 and stripping vapor for the high pressure section 14 in conjunction with the feed gas in line 10. The carbon dioxide and $C_1$ and $C_2$ hydrocarbons are generally vaporized subsequent to the flash in valve 36 and removed to the high pressure section 14. This separation reduces the duty necessary on the reboiler 52 of the low pressure section 16. Because the flash occurs at generally low temperatures, the removal of propane and higher hydrocarbons into the return to the high pressure section is minimized and the concentration of those components as reflux to the low pressure section 16 is maximized.

The low pressure section 16 produces a bottom stream 50 which comprises predominantly heavy hydrocarbons and solvent with little carbon dioxide and $C_1$ or $C_2$ hydrocarbons. This bottom stream 50 is introduced into a reboiler 52 which provides low heat duty reboil under less rigorous conditions than conventional practice due to the initial separation between the high pressure and low pressure sections and because of the low pressure existing in the low pressure section 16. This low pressure allows for the more volatile light component materials to more easily vaporize under the reboiling conditions of reboiler 52. These components are returned in line 54 to the low pressure section 16 as reboil to that section of the column. The reboiler is operated by indirect heat exchange with a regenerated and recycled solvent stream from a downstream solvent recovery column. In most cases, no additional energy input to the reboiler is deemed necessary. The heavy components, which are less volatile, such as the propane and higher hydrocarbons as well as the solvent are removed from the reboiler in line 56 and reduced in pressure in valve 58 before introduction into a solvent recovery column 60, being the second distillation column of the process.

The solvent regeneration is performed by reducing the pressure from approximately 200 psia down to 100 psia through valve 58. Typically, the pressure of regeneration is in the range of 20–150 psia. Alternatively, the temperature could be raised to effect the same result. The column 60 performs a stripping action whereby the propane and higher hydrocarbons are stipped into the vapor phase from the action of the reboiling vapor which has a temperature of approximately 400° F. This reboil is effected by removing a bottom stream in line 70 and reboiling it in reboiler 72 which is heated by a fuel-fired combustion process 76. The preferred fuel would be natural gas combusted with air. This high temperature reboil action effects a separation of the solvent, which is removed as a bottom stream in line 78 being fully regenerated and lean with respect to the absorbed components in the extractive distillation column, and a stripping vapor stream in line 74 which is reintroduced into the solvent recovery column 60 as reboil for that column. The lean, hot solvent in line 78 provides heat duty by indirect heat exchange in the reboiler 52 before being removed in line 80 and cooled against external cooling fluid in heat exchanger 82, such as ambient water. It is then combined with any necessary makeup solvent from line 84 before being pumped to elevated pressure by pump 86 through line 88 and further cooled in heat exchanger 30 before final introduction as extractive solvent in line 26 into the high pressure section 14 of the extractive distillation column 12.

The propane and higher hydrocarbons which have been volatilized with respect to the extractive solvent in the solvent recovery column 60 are removed in line 62 as an overhead vapor stream and are introduced into a condenser 64 wherein any vaporized solvent is returned as reflux to the column 60 in line 66. The resulting heavy component product is removed in line 68 and has a composition with generally makes it meet the specifications for natural gas liquids or NGL. This product comprises propane and higher hydrocarbons which are essentially free of light hydrocarbons, such as methane and ethane, and extractive solvent, such as lower alkanes and siloxane components depending upon the particular extractive solvent utilized for the process. The product typically has a carbon dioxide content of 5-15 mole %.

The present invention has been described with regard to one preferred embodiment of the invention. It is understood that those skilled in the art will be able to contemplate obvious varients from this embodiment which varients are deemed to be within the scope of the invention, which scope should be ascertained from the claims which follow.

We claim:

1. A method for the extractive distillation of a feed gas stream into several products comprising the steps of:
   (a) introducing a feed gas containing multiple separable components into the high pressure section of a two pressure section extractive distillation column;
   (b) contacting the feed gas with an extractive solvent to assist in the separation of the multiple components of the gas;
   (c) cooling the overhead of said high pressure section to condense a liquid phase reflux to the high pressure section of the column and to recover a substantially pure light component product stream;
   (d) removing a bottom stream from said high pressure section and reducing the pressure of said bottom stream to phase separate a vapor reboil stream to said high pressure section and a liquid reflux feed stream to a low pressure section of said column;
   (e) introducing said liquid reflux feed stream into the low pressure section of said two pressure section extractive distillation column;
   (f) removing a light component stream from the overhead of said low pressure section, repressurizing the same and introducing it into the high pressure section;
   (g) reboiling said low pressure section to provide vapor reboil for said low pressure section and a liquid heavy component solvent stream; and
   (h) introducing the heavy component solvent stream into a second column and separating the stream into the heavy components as a product and the solvent as a recycle extractive solvent to the two pressure section extractive distillation column.

2. The method of claim 1 wherein the feed gas is a mixture of carbon dioxide and hydrocarbons which is separated into a carbon dioxide and light hydrocarbons up to $C_2$ as a light component product and $C_3$ and heavier hydrocarbons as a heavy component product.

3. The method of claim 1 wherein the extractive solvent is selected from the group comprising $C_3-C_8$ hydrocarbons and silicon containing hydrocarbons.

4. The method of claim 1 wherein the extractive solvent is a siloxane.

5. The method of claim 1 wherein the pressure of the high pressure section of the two pressure section distillation column is in the range of 250-500 psia.

6. The method of claim 1 wherein the pressure of the low pressure section of the two pressure section distillation column is in the range of 50-300 psia.

7. The method of claim 1 wherein the solvent from the second column reboils the low pressure section by indirect heat exchange, is cooled against light component product and is introduced into the upper part of the high pressure section of the two pressure section distillation column.

8. The method of claim 1 wherein the light component stream from the low pressure section is mixed with the vapor reboil stream to the high pressure section, the combined stream is pressurized to the pressure of the high pressure section and the combined stream is introduced into the high pressure section.

9. A method for the extractive distillation of a carbon dioxide and hydrocarbon containing feed gas stream into a light product including carbon dioxide and hydrocarbons up to approximately $C_2$ and a heavy product including $C_3$ and heavier hydrocarbons comprising the steps of:
   (a) introducing a feed gas containing carbon dioxide and hydrocarbons into the high pressure section of a two pressure section extractive distillation column wherein the high pressure section operates at about 250-500 psia;
   (b) contacting the feed gas with an extractive solvent comprising $C_3-C_8$ hydrocarbons or a siloxane to assist in the separation of the multiple components of the gas;
   (c) cooling the overhead of said high pressure section to condense a liquid phase reflux to the high pressure section of the column and to recover a substantially pure light component product stream of carbon dioxide and up to approximately $C_2$ hydrocarbons;
   (d) removing a bottom stream from said high pressure section and reducing the pressure of said bottom stream to phase separate a vapor reboil stream to said high pressure section and a liquid reflux feed stream to a low pressure section of said column operating at about 50-300 psia;
   (e) introducing said liquid reflux feed stream into the low pressure section of said two pressure section extractive distillation column;
   (f) removing a light component stream from the overhead of said low pressure section, repressurizing the same and introducing it into the high pressure section;
   (g) warming said low pressure section by heat exchange with said extractive solvent in order to provide a vapor reboil stream to said low pressure section and a liquid heavy component solvent stream; and
   (h) introducing the heavy component solvent stream into a second column and separating the stream into the heavy components as a $C_3$ and heavier hydrocarbon product and the solvent as a recycle extractive solvent to the two pressure section extractive distillation column.

10. An apparatus for the extractive distillation of a multiple component feed gas stream into a light component product and a heavy component product comprising:
    (a) an extractive distillation column with a high pressure section and a low pressure section;
    (b) a condenser for the high pressure section;
    (c) a reboiler for the low pressure section;
    (d) means for flashing and separating a bottom stream from said high pressure section to form a reboil stream for the high pressure section and a reflux stream for the low pressure section;
    (e) a second column for separating extractive solvent from heavy component product, and
    (f) means for circulating extractive solvent from said second column, through said reboiler in indirect heat exchange, and to said extractive distillation column.

11. The apparatus of claim 10 including means for removing light components from the overhead of the low pressure section and introducing the same into the high pressure section.

* * * * *